(12) United States Patent
McInnes (10) Patent No.: US 6,558,405 B1
(45) Date of Patent: May 6, 2003

(54) EMBOLIC FILTER

(75) Inventor: Peter R. McInnes, Encinitas, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/650,278

(22) Filed: Aug. 29, 2000

(51) Int. Cl.[7] .............................................. A61M 29/00

(52) U.S. Cl. ..................................................... 606/200

(58) Field of Search ............................... 606/200, 127, 606/114, 159, 1

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |

(List continued on next page.)

FOREIGN PATENT DOCUMENTS

| | | |
|---|---|---|
| EP | 0 472 334 A1 | 2/1992 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |

*Primary Examiner*—Kevin T. Truong
(74) *Attorney, Agent, or Firm*—Fulwider Patton Lee & Utecht, LLP (57) ABSTRACT

An intravascular filter for capturing embolic particles entrained in blood flowing in an arterial vessel during an interventional procedure. The filter is intended to be used as a primary filtering device in conjunction with interventional treatment procedures such as balloon angioplasty and/or stenting. The filter may also be used as a secondary filtering device in conjunction with suction in atherectomy and other interventional procedures. The filter is capable of capturing embolic particles at least as small as 150 microns in diameter, thereby increasing the safety of balloon angioplasty and stenting. The filter includes a spring-like expandable strut assembly and a filtering medium composed of a plurality of complex passageways. The filter assembly is compressible to an initial low profile delivery diameter and is expandable to a larger deployed diameter.

53 Claims, 3 Drawing Sheets

U.S. PATENT DOCUMENTS

| | | | |
|---|---|---|---|
| 5,330,482 A | 7/1994 | Gibbs et al. |
| 5,350,398 A | 9/1994 | Pavcnik et al. |
| 5,370,657 A | 12/1994 | Irie |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maahs |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,941,896 A | 8/1999 | Kerr |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,013,093 A | 1/2000 | Nott et al. |
| 6,066,158 A * | 5/2000 | Engelson et al. | 606/200 |
| 6,152,946 A | 11/2000 | Broome et al. |
| 6,171,327 B1 | 1/2001 | Daniel et al. |
| 6,179,859 B1 * | 1/2001 | Bates et al. | 606/200 |
| 6,319,242 B1 | 11/2001 | Patterson et al. |
| 6,346,116 B1 | 2/2002 | Brooks et al. |

* cited by examiner

EMBOLIC FILTER

BACKGROUND OF THE INVENTION

The present invention relates generally to the field of percutaneous transluminal treatment of stenosed or narrowed arteries in the human vascular system. More particularly, the invention is directed to an embolic filter for capturing particles dislodged from a stenosis during an interventional procedure performed to improve blood flow through the stenosed artery.

Arteries can become stenotic in a number of ways. Often, a stenosis or lesion forms due to an accumulation of atherosclerotic plaque on the walls of a blood vessel. Atherosclerotic plaque can take many forms, one of which is a hard calcified substance, particles of which tend to dislodge during interventional procedures and embolize or flow freely in the circulatory system. A stenosis may also form from an accumulation of thrombus material which is typically softer than atherosclerotic plaque, but can nonetheless cause restricted blood flow in the lumen of a vessel. Like atherosclerotic plaque, thrombus material also tends to dislodge during interventional procedures. As used here, the term emboli refers to free flowing particulates whether composed of plaque, thrombus, or another material. Such free flowing emboli are dangerous since they may become lodged in a small blood vessel and occlude or partially occlude the vessel.

Various approaches have been developed to treat a stenotic lesion in the vasculature. Among the most common are balloon angioplasty and atherectomy. Balloon angioplasty is directed towards relieving the constriction in the artery by radially expanding the stenosis against the artery wall, while atherectomy attempts to remove the stenosis from the artery.

In a typical balloon angioplasty procedure, a guiding catheter is percutaneously introduced into the cardiovascular system of a patient through the femoral arteries by means of a conventional Seldinger technique and advanced within a patient's vascular system until the distal end of the guiding catheter is positioned at a point proximal to the lesion site. A guide wire and a dilatation catheter having a balloon on the distal end are introduced through the guiding catheter with the guide wire sliding within the dilatation catheter. The guide wire is first advanced out of the guiding catheter into the patient's vasculature and is directed across the arterial lesion. The dilatation catheter is subsequently advanced over the previously advanced guide wire until the dilatation balloon is properly positioned across the lesion. Once in position, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter may be withdrawn from the patient's vasculature and the blood flow resumed through the dilated artery. As should be appreciated by those skilled in the art, while the above-described procedure is typical, it is not the only method used in angioplasty.

The procedure for atherectomy is similar to that of balloon angioplasty in that a guiding catheter is introduced into the patient's vasculature through a conventional Seldinger technique and a guide wire is typically advanced through the guiding catheter and across an arterial lesion to a point distal of the lesion. However, rather than expanding the lesion with a balloon, in atherectomy, a specialized catheter containing rotating cutting blades is used to mechanically cut or abrade the stenosis from the artery wall.

With both of the above procedures, the treated artery wall suffers a degree of trauma and in a small percentage of cases may abruptly collapse or may slowly narrow over a period of time. To prevent either of these conditions, the treatment procedure may be supplemented by implanting within the arterial lumen a prosthetic device known as a stent. A stent is a small tubular metallic structure which is fitted over a catheter balloon and expanded at the lesion site. Stents serve to hold open a weakened blood vessel and prevent the blood vessel from narrowing over time. Balloon angioplasty, atherectomy, and stenting procedures have proven successful and are widely used in the treatment of stenosis of the coronary and peripheral arteries and have for many patients rendered unnecessary invasive bypass surgery. However, all of the above procedures tend to create embolic particles which, in certain arteries, such as the carotid arteries, create a risk of ischemic stroke. For this reason, these beneficial techniques are rarely used in treating the carotid arteries, leaving invasive endarterectomy surgery as the primary treatment choice.

Embolic particles may be created during balloon angioplasty because stenoses are often formed from hard calcified plaque which tends to crack upon radial expansion. Upon cracking, emboli may be released into a patient's bloodstream. Emboli may also be formed during a stent placement procedure as the metal struts of the stent may cut into the stenosis and shear off plaque or thrombus material. During an atherectomy procedure, for example, a constant stream of particles is cut from the stenosis which may not be totally captured by the mechanical filters or suction devices used in conjunction with this procedure. Thus, some particles are not captured and flow downstream as embolic. Certain locations in the patient's vasculature can provide an even greater chance of creating friable plaque which can dislodge and enter the patient's bloodstream. For example, saphenous vein grafts are of a special concern to the interventionalist. Disease in these grafts is typically a very friable plaque that can dislodge quite easily. For example, the mere act of passing the interventional devices through these vessels can dislodge embolic material which will be released into the patient's bloodstream. When a physician performs a procedure in the saphenous vein, a filtering system which can capture the friable plaque is greatly needed.

Numerous embolic filters or traps for deployment distal of a lesion site have been proposed. The majority of these devices use some form of woven wire mesh basket to capture emboli, where the mesh is composed of square or diamond shaped cells. A typical example of the wire mesh basket type of intravascular filter is described in U.S. Pat. No. 4,873,978, entitled "Device and Method for Emboli Retrieval" issued to Ginsburg. Ginsburg discloses a removable vascular filter permanently attached to a guide wire for deployment from a catheter. The filter is comprised of an expandable wire mesh basket employing diamond shaped cells. Upon deployment, the filter expands to contact the walls of the lumen, thereby obstructing the vessel and straining blood flowing through the lumen.

A variation of the wire mesh basket approach is described in U.S. Pat. No. 5,152,777, entitled "Device and Method for Providing Protection From Emboli and Preventing Occlusion of Blood Vessels" issued to Goldberg et al. This device consists of a filter having a plurality of resilient, stainless steel wire arms joined at one end so as to form a conical surface, and having rounded tips at their other ends to prevent damage to the vessel walls. Each arm is wound with wire in a form similar to a coil spring. Goldberg proposes that emboli entrained in blood flowing past the spring arms will be caught in the coils of the arms.

Prior art wire mesh filters have several drawbacks. The most significant of which is the relatively large cell size of the mesh. Embolic particles with nominal diameters larger than 150 microns pose a serious risk of occluding or partially occluding fine vasculature. A very fine wire mesh basket may have cells with openings about 3000–4000 microns on a diagonal across the square or diamond shaped cell. Thus, wire mesh filters may be unable to trap such small embolic particles and may be unsuitable for use in the treatment of lesions in the carotid arteries where emboli produced by an interventional procedure have a short flow path to the small diameter vessels of the brain. Moreover, other drawbacks of these types of filtering includes relatively high pressure drop, which increases with finer mesh sizes. These devices also have limited capacity as the fine pores can become clogged relatively quickly.

What is needed is a reliable filtering device that may be placed distal of an arterial lesion and used in conjunction with balloon angioplasty, atherectomy, stenting, or other interventional procedures. The device should be able to reliably trap any embolic debris with a nominal diameter larger than 150 microns and thereby render the above named procedures safe for treating lesions in the carotid arteries. Further, the device should be relatively easy to deploy and remove from the patient's vasculature. The present invention meets these and other needs.

SUMMARY OF THE INVENTION

The present invention provides an improved intravascular filter for capturing embolic particles entrained in blood flowing in an arterial vessel during an interventional procedure. The filter is intended to be used as a primary filtering device in conjunction with interventional treatment procedures such as balloon angioplasty and/or stenting. The filter may also be used as a secondary filtering device in conjunction with a suction catheter in atherectomy and other stenosis removal procedures. The filter is capable of capturing embolic particles at least as small as 150 microns in diameter, thereby dramatically increasing the safety of balloon angioplasty and stenting. As a result, balloon angioplasty and stenting may be more frequently used in the carotid arteries where the risk of stroke from embolic particles is exceptionally high.

The filter of the present invention includes a strut assembly and a filtering medium. The strut assembly is compressible to an initial low profile delivery diameter and is expandable to a larger deployed diameter. The strut assembly is composed of a plurality of struts which may be made, for example, from spring steel or from a shape memory alloy. More specifically, the strut assembly includes an elongated cylindrical center portion and conical end portions which are shaped as truncated cones, terminating at proximal and distal collars. Attached to the strut assembly is the filtering medium which may be formed from either an open cell, porous, bio-compatible polymer foam, or a felted polymer fabric.

The filter element operates as a depth filter where embolic particles are trapped within the pores of the filter medium. Depth filters allow a high blood flow rate as well as fine filtration by utilizing layered filter media. In one embodiment, the filter element includes three media layers of depth filter. The top layer serves to capture large particles while presenting minimal resistance to blood flow. The second layer has a density greater than the first layer to capture smaller embolic particles. The bottom layer has even a greater density than the preceding layers to capture even smaller embolic particles. The bottom layer captures very fine embolic particles, however, due to its thinness and the fact that it receives blood substantially free of large embolic particles, the bottom layer does not significantly impede blood flow therethrough. Thus, the filter of the present invention may capture extremely small diameter embolic particles while still allowing a sufficient quantity of blood flow to prevent ischemic. Moreover, the depth filter, which relies on a "web" of media that has a certain density, creates a filtration device which helps prevent the embolic particles from being released from the filter as the filter is being removed from the patient's vasculature. This is due to the fact that the particles become entrapped in this "web" of media and become somewhat entangled in the filter. In an embolic filtering device which utilizes, for example, a sheet of filtering material, rather than a web, there is a chance that the emboli can be "backwashed" into the patient's bloodstream as the filter is being collapsed for withdrawal from the body lumen. This scenario is actually detrimental to the patient since emboli which should have been captured by the filter are now released into the bloodstream.

The filter may be delivered to a desired location within an artery by means of a guide wire and a delivery sheath. The filter can be rotatably attached to the guide wire by the proximal collar of the strut assembly. The distal collar of the strut assembly slides axially over the guide wire and is also rotatable on the guide wire as well. This allows the strut assembly to move between its collapsed and expanded positions while still allowing the filter to freely rotate or "spin" about the guide wire. The attachment of the proximal collar of the strut assembly to the guide wire allows the restraining sheath to be retracted from the filter and permits a recovery sheath to be placed over the expanded strut assembly to move the strut assembly back to the collapsed position when the embolic protection device is to be removed from the patient's vasculature.

Other features and advantages of the present invention will become more apparent from the following detailed description of the invention, when taken in conjunction with the accompanying exemplary drawings.

DETAILED DESCRIPTION OF THE PREFERRED EMBODIMENTS

The filter of the present invention is described as being used in conjunction with a balloon angioplasty procedure. The filter, however, is not intended to be limited to use with balloon angioplasty procedures, rather it may be used in any interventional procedure where it is important to trap and remove fine particles of embolic material.

Figure 1:
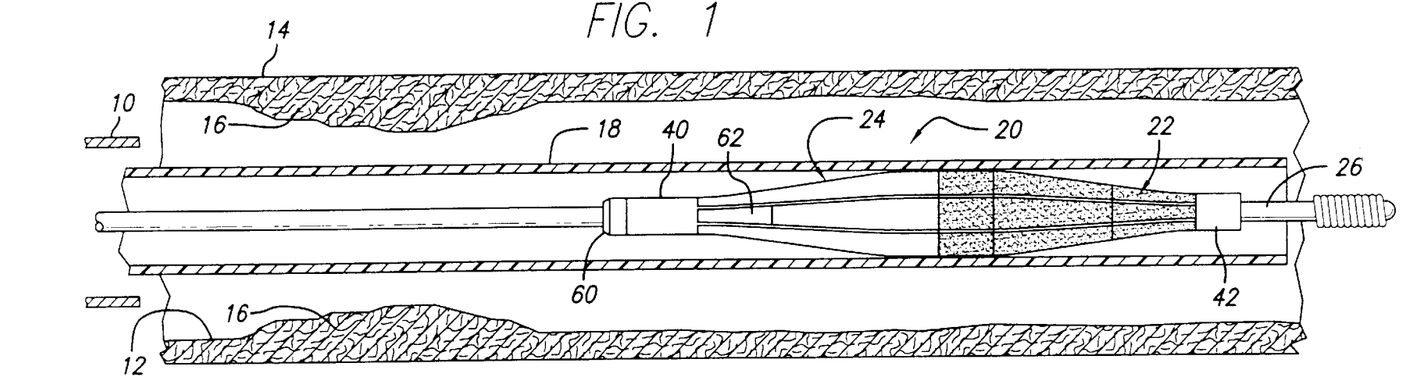
FIG. 1 is an elevational view, partially in cross section, of an embolic protection device embodying features of the present invention showing the expandable filter in its collapsed position within a restraining sheath and disposed within a vessel.

Referring now to FIG. 1, a guiding catheter 10 has been percutaneously introduced into a patient's vascular system by means of a conventional Seldinger technique and advanced through a lumen 12 of an arterial vessel 14, to a position proximal of an arterial lesion 16. A delivery sheath 18, which has been previously loaded with an emboli filter 20 in accordance with the present invention, and a guide wire 26, have been advanced to a point where the filter is positioned distal of the arterial lesion. The filter 20 is shown in its collapsed or low profile position and includes a filtering element 22 and an expandable strut assembly 24. The filter is rotatably mounted on the distal end of a guide wire 26. Upon positioning the filter distal of the lesion, the delivery sheath is retracted, thereby deploying the filter within the lumen of the arterial vessel. The deployed filter is depicted in FIG. 2.

Figure 2:
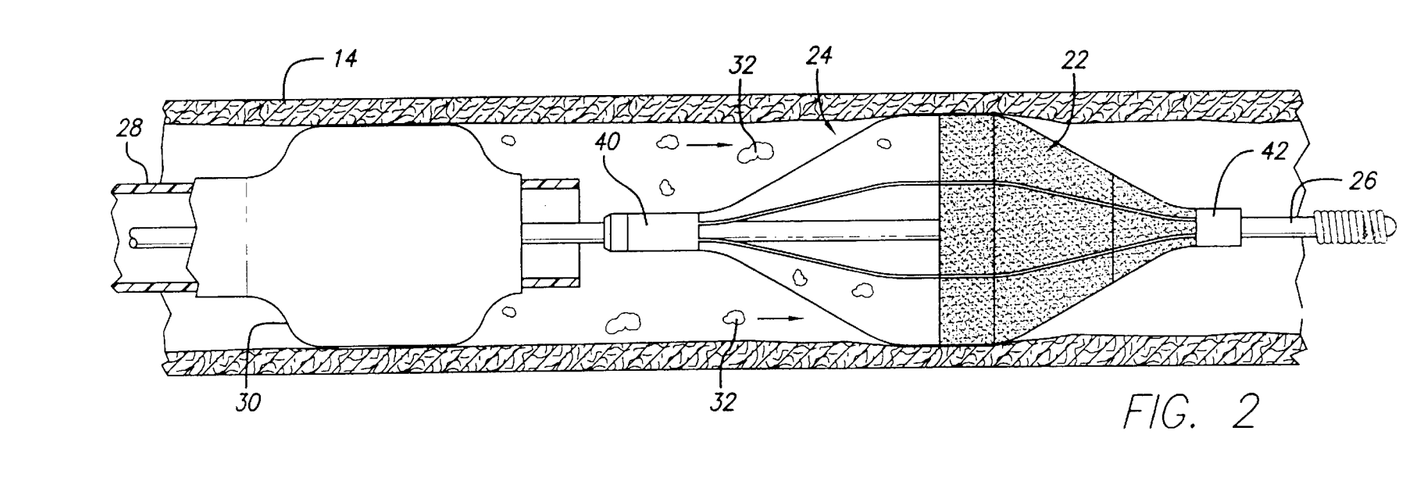
FIG. 2 is an elevational view, partially in cross section, similar to that shown in FIG. 1, wherein the expandable filter is in its expanded position within the vessel.

Referring now to FIG. 2, subsequent to deployment, the delivery sheath 18 is withdrawn from the guiding catheter 10 and a balloon dilatation catheter 28 having an inflation balloon 30 is advanced over the guide wire 26 to a position across the lesion 16. Once in position across the lesion, the balloon is expanded with radiopaque fluid at high pressure, thereby radially expanding or dilating the arterial lesion. Upon dilation, the hard calcified atherosclerotic plaque which forms the lesion may crack and form embolic particles or emboli 32. The emboli flowing downstream of the dilated lesion are captured by the filtering element 22 of the filter 20. Once the angioplasty procedure is complete, the balloon catheter is removed and may, as determined by the treating physician, be followed by a stent-delivery catheter (not shown) for placement of a stent across the dilated lesion. The stent placement procedure may also form embolic particles which would be captured by the filter. Once the angioplasty and/or stenting procedure is completed a retraction sheath (not shown) is introduced into the guiding catheter and advanced to a point distal of the lesion and proximal of the filter. The filter is subsequently withdrawn into the retraction sheath and the sheath, filter, guide wire, and embolic debris captured by the filter are withdrawn from the patient.

Figure 3:
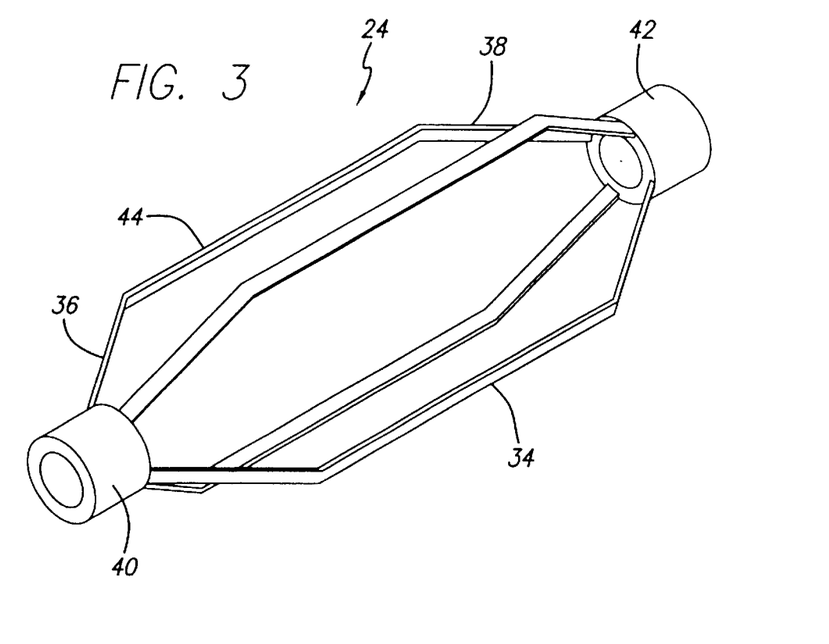
FIG. 3 is a perspective view of the strut assembly which forms part of the filter of the present invention as shown in its expanded position.

Referring now to FIGS. 1–4, the expandable strut assembly of the filter possesses spring-like or self expanding properties and can move from a compressed or collapsed position as shown in FIG. 1 to an expanded or deployed position shown in FIG. 2. With particular reference to FIG. 3, the strut assembly includes an elongated cylindrical center portion 34 and proximal and distal end portions 36 and 38 which are shaped as truncated cones, terminating at proximal and distal, hollow, cylindrical, guide wire collars 40 and 42. Starting from the proximal collar 40, the strut assembly comprises a plurality of individual struts 44 which taper upward to form the proximal truncated cone portion 36 of the of the strut assembly. The struts 44 continue, extending longitudinally, to form the elongated, straight, center portion 34 of the strut assembly. The struts then taper downward forming the distal truncated cone portion 38 of the strut assembly and terminate at the distal collar. While the figures show only four individual struts, the invention is not limited to this configuration as strut assemblies containing six or eight or more struts are practical.

The strut assembly 24 may be produced by several methods including electro-discharge machining and chemical etching. However, the preferred method is to laser machine a thin-walled tubular member, such as a hypotube. In this procedure, a computer controlled laser cuts away portions of the hypotube following a pre-programmed template to form the desired strut pattern. Methods and equipment for laser machining small diameter tubing are well known in the prior art.

The tubing used to make the strut assembly may be made of any bio-compatible spring steel or shape memory alloy. The 300 series stainless steel alloys are well suited to this application with type 316L stainless steel per ASTM F138-92 or ASTM F139-92 grade 2 being preferred. Of the shape memory or super-elastic alloys, Nitinol a 55% nickel–45% titanium alloy is preferred. Other shape memory alloys such as Ni—Ti—X (X being V, Co, Cu, Fe) ternary alloys, Cu—Al—Ni ternary alloys and Cu—Zn—Al ternary alloys are also suitable.

Typically, suitably sized tubing for making the strut assembly 24 will have an outer diameter on the order of about 0.020–0.040 inches, with a wall thickness of about 0.003–0.006 inches. However, tubing size will vary depending upon the application. It is preferred that the strut assembly be machined from seamless tubing. However, tubing formed by rolling flat, sheet stock into a cylinder with welded longitudinal edges is also suitable as is rolled sheet stock which has been drawn through a circular die.

Figure 5:
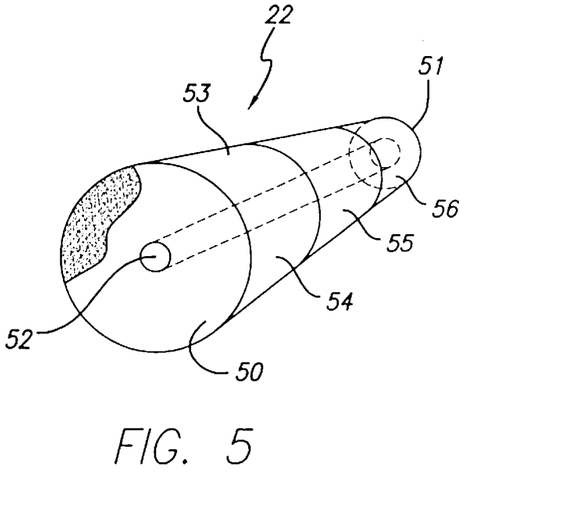
FIG. 5 is a perspective view of another filter element embodying features of the present invention.

Referring now to FIG. 5, in one embodiment, the filtering element 22 has a body 53 formed as a truncated cone which includes an inlet face 50, an outlet face 51 and a through bore 52 for the guide wire 26. The body can be formed from a compressible, porous polymer foam, such as thermally reticulated polyurethane foam. Open cell foam materials are porous and provide a plurality of complex passageways which may be utilized to capture embolic particles. Other bio-compatible polymer materials which may be foamed, such as polyester, are also suitable. The filter element body may have a top layer 54, an intermediate layer 55 and a final filtration layer 56, where each succeeding foam layer has a mean pore size smaller than that of the preceding layer.

In one embodiment, the top or initial filtering layer 54 has a filter media density which results in a mean pore size of about 1000 microns for coarse filtering of large embolic particles. Layer 54 is the thickest layer and presents the least resistance to blood flow. The intermediate layer 55 can have a filter media density which results in about 500 microns and is proportionately less thick than the preceding layer 54. Layer 54 is capable of removing most emboli large enough to pose a threat to the patient. The last filtration layer 56 has a filter media density which results in a mean pore size of about 100 microns. This final layer serves to filter out very fine embolic particles that may have passed through the previous layers and is comparatively thin so as not to unduly restrict blood flow through the filter. This thickness of the various layers can be varied to suit the needs of individual device performance requirements. While three filtration layers are illustrated in FIG. 5, the actual number of layers may vary depending upon the intended application. In some applications, the filter body 53 may consist of a single layer with a uniform mean pore size. In certain, specialized applications, the number of filter layers may exceed three. Hence, the above example is meant to exemplary only.

Figure 4:
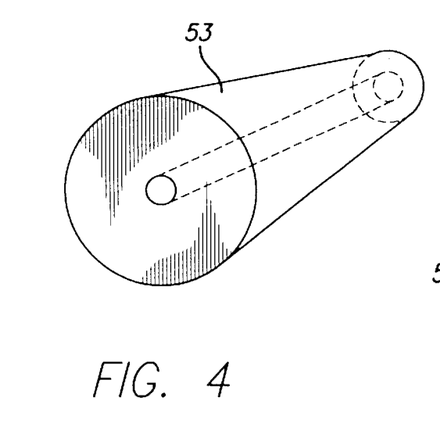
FIG. 4 is a perspective view of a filter element embodying features of the present intention.

Referring now to FIG. 4, in another embodiment, the filter element 22 may comprise a felt made of bio-compatible synthetic fibers. Suitable fiber materials are polypropylene and polyester. Many other bio-compatible polymers such as, polyamide, polyethylene, PTFE, and polyolefin are also suitable. The filter element 22 may comprise a single felt layer having an inlet surface 50 and an outlet surface 51 or the filter element 22 may comprise a top felt layer, a bottom felt layer, and a plurality of layers therebetween. Like an open cell foam material, felt also provides a system of complex pathways which act to filter particulate matter in a patient's blood. Felts may be obtained in a wide range of densities. Felts composed of about 1 to 3 denier fiber having a weight of about 8 to 10 ounces per square yard are approximately equivalent to foams with a mean pore size of about 50 to 200 microns. Felts within this range are well suited for use as the filter element 22 of the present invention. Therefore, a filter constructed of multiple felt layers similar to the foam filter described above, may also have layers of varying porosity, where the lower layers are of finer porosity than the upper layers. Filter elements made in accordance with the present invention can be made from material as which approximate materials used in arterial blood filters or cardiotomy filters for bypass surgery.

An advantage of both felt and porous foam filter elements is that embolic particles are trapped within the fibers in the case of felts and within the pores in the case of foams. Once trapped there is little risk of the particles escaping the fibers or pores upon withdrawal of the filter.

If desired, a filter element 22 in accordance with the present invention could capture extremely fine embolic debris. For example, bypass filters capable of filtering embolic in the 20–100 micron range could be utilized. However, it is believed that embolic particles smaller than about 150 microns are unlikely to occlude or partially occlude a blood vessel branching from a critical artery, such as the carotid arteries. Thus, the presently preferred lower limit for the mean pore size of either the foam or felted filter element is about 100 microns. Other considerations also effect the mean pore size. Small pores result in reduced blood flow downstream of the filter. Low blood flow could result in ischemia with adverse effects on the patient. This situation is particularly critical in the carotid arteries where blood starvation may lead to oxygen deprivation in the patient's brain, a highly undesirable condition. Thus, the filter pore size should be chosen with regard to the intended application. For example, in the coronary arteries where the risk of stroke is lower than in the carotid arteries it may be desirable to use a lower limit pore size larger than 100 microns to improve blood flow through the filter.

The filter element 22 may be attached to the strut assembly 24 by any known method, such as adhesive bonding. The adhesive may be a thermoplastic adhesive and preferably a thermoplastic fluoropolymer adhesive such as fluorinated ethylene propylene ("FEP").

Referring now to FIGS. 1–2 and 6–7, the filter 20 is rotatably secured to a shaft member such as the guide wire 26 as follows. The filter is slid onto the guide wire with the guide wire sliding within the proximal and distal collars 40 and 42. The proximal collar 40 of the expandable strut assembly 24 is mounted between a tapered fitting 60 located proximal of the collar 40 and a radiopaque marker band 62 located distal of the collar 40. The tapered end fitting 60 and marker band 62 fix the proximal collar 40 onto the guide wire to prevent any longitudinal motion of the proximal collar along the guide wire but allow for rotation of the proximal collar and of the filter 20 about the guide wire. This particular construction allows the expandable strut assembly to rotate or "spin" freely about the guide wire while allowing the strut assembly to move longitudinally along the guide wire at the distal collar 42. The above example is merely illustrative of one method of rotatably attaching the filter 20 to the guide wire. Other ways of performing this same function can be employed with the present invention.

Figure 6:
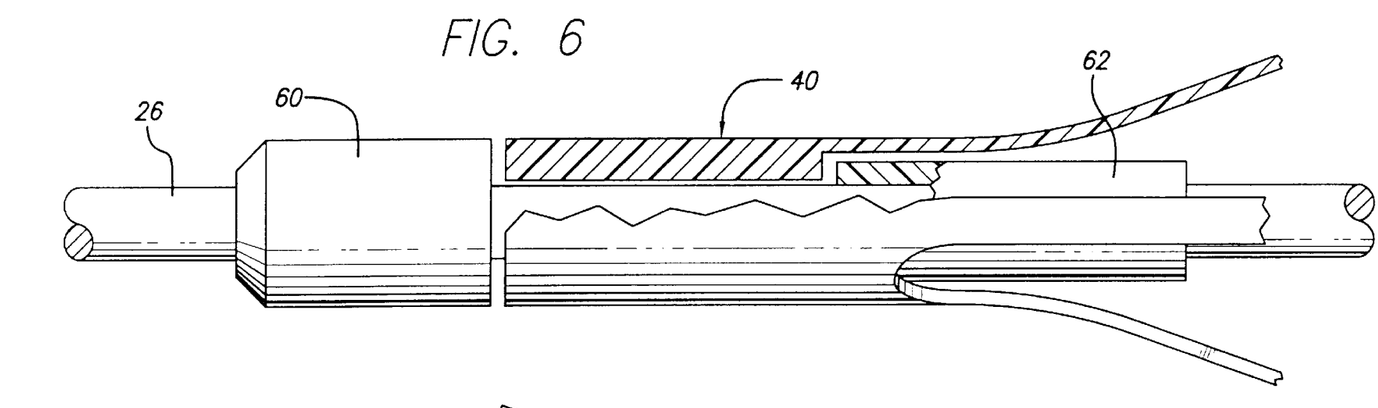
FIG. 6 is an elevational view, partially in cross section, of the proximal end of the expandable strut assembly of FIG. 2 as it is rotatably attached to the guide wire.
Figure 7:
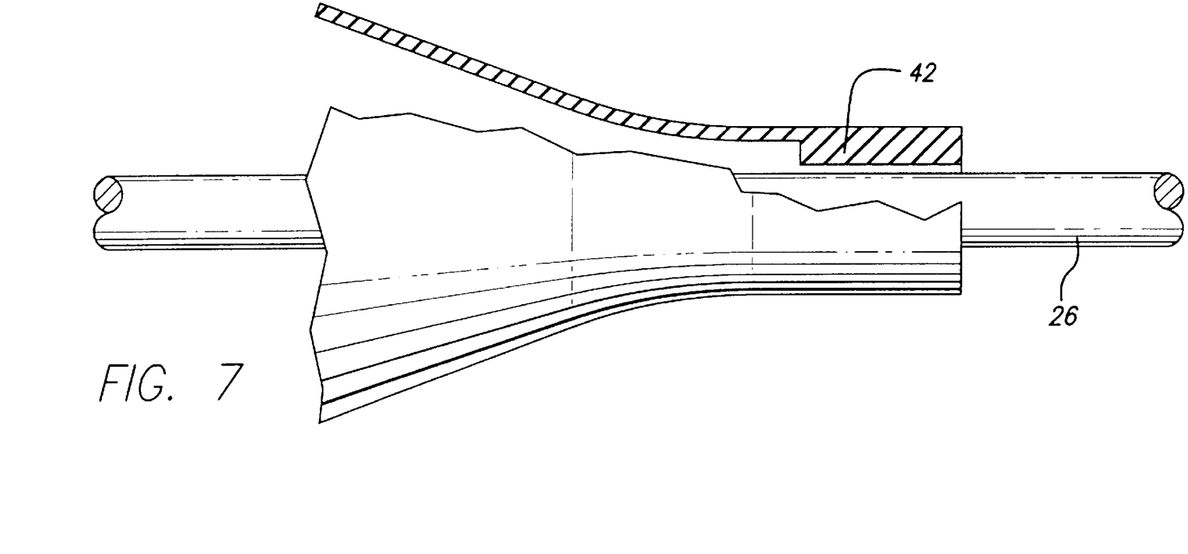
FIG. 7 is an elevational view, partially in section and fragmented, showing the distal end of the filtering assembly of FIG. 2 as it is slidably mounted on the guide wire.

By rotatably mounting the filter 20 to the guide wire in the manner described, the filter will lengthen longitudinally with the distal collar 42 sliding along the guide wire when the strut assembly is compressed for insertion into the delivery sheath 18. Likewise, the filter will contract longitudinally while its expands radially upon release from the delivery sheath and deployment within the vessel lumen 12. An advantage of rotatably mounting the filter on the guide wire is that the filter will remain stationary should the guide wire be rotated at its proximal end after the filter has been deployed within the patient's vasculature. If the filter were to rotate after deployment, damage to the vessel lumen may occur.

With reference to FIGS. 1 and 2, after the filter 20 has been attached to the guide wire 26, the filter may be prepared for use by threading the proximal end of the guide wire through the distal end of the delivery sheath 18 and subsequently compressing and sliding the filter into the sheath. This manner of loading the filter is referred to as backloading. The filter may be front-loaded into the sheath by threading the distal end of the guide wire and the filter through the proximal end of the delivery sheath, however, the delivery sheath is typically about 135 cm long and forcing the filter to travel the full length of the sheath may tear or otherwise damage the filter element 22. Thus, backloading is the preferred procedure. After loading, the delivery sheath is advanced through the pre-positioned guiding catheter 10 to a point distal of lesion 16. The filter is deployed by simply pushing it out of the sheath by means of the guide wire. After deployment from the sheath, the spring-like strut assembly 24 expands against the lumen wall 12, forcing blood to be strained through the filter. At this point, the filter is fully functional and the desired interventional procedure may be performed.

After the interventional procedure is completed and any associated equipment removed, the filter 20 may be withdrawn as follows. A recovery sheath (not shown) is advanced through the guiding catheter 10 to a point just proximal of the filter. Generally, this recovery sheath has a slightly larger inner diameter than the delivery sheath 18 since the struts 44 are now deployed and the recovery sheath may require increased hoop strength at its distal end to properly move the strut assembly 24 back into its collapsed position. Compression of the expandable strut assembly can be accomplished by holding the guide wire 26 and moving the proximal end of the recovery sheath forward which will move the distal end of the sheath over the struts. Alternatively, the recovery sheath can be held stationary while the proximal end of the guide wire is retracted to pull the filter assembly into the sheath. Upon collapse of the filter assembly, any embolic debris generated and entering the bloodstream during the interventional procedure will remain trapped inside the filtering element 22 and will be withdrawn from the bloodstream when the filter is removed from the patient's vasculature.

It should be appreciated that other mechanical devices can be utilized in deploying the filtering element made in accordance with the present invention. For example, the strut assembly could be made with individual struts which are operable between a collapsed and retracted position by manipulation of the proximal end of the guide wire onto which the assembly is mounted. In this embodiment, rather than utilizing self-expanding material as described above, a non-self-expanding material can be utilized. This mechanism can be manually operated by a physician to open and close the struts of an assembly similar to the one shown in FIGS. 1–3. For example, the proximal collar 40 of the strut assembly shown in FIG. 1 could be attached to a tubular member which extends coaxially over the guide wire 26 to a position outside of the patient. The distal collar 42 would be permanently attached to the guide wire. Of course, the tapered end fitting 60 and marker band 62 would have to be removed in such an embodiment to allow the proximal collar 40 to move axially along the guide wire 26 to move the struts between the expanded and collapsed positions. The physician would move the proximal ends of the guide wire and the outer tubular member relative to one another in order to push the struts to the expanded or collapsed position, thus opening and closing the filtering element within the patient's vasculature. This is but one example of the mechanical assembly which could be utilized in conjunction with a filtering device of the present invention in order to possibly deploy the filter within the patient's vasculature. To those skilled in the art, other mechanical devices could be utilized to deploy the filtering element within the patient's vasculature without departing from the spirit and scope of the present invention.

It will be appreciated that a new intravascular filter for capturing embolic particles formed during an angioplasty or other interventional procedure has been presented. The filter is capable of capturing fine embolic particles, thereby improving the safety of these procedures particularly when they are employed in critical arteries such as the carotid arteries. While only the presently preferred embodiments have been described in detail, as will be apparent to those skilled in the art, modifications and improvements may be made to the device and method disclosed herein without departing from the scope of the invention. Accordingly, it is not intended that the invention be limited, except as by the appended claims.

What is claimed is:

1. A filter device for capturing embolic particles released into a body lumen of a patient, comprising:
   an expandable strut assembly, the expandable strut assembly having a plurality of expandable struts adapted to move between a collapsed position and an expanded position;
   a filtering element having an inlet face and an outlet face and including a plurality of layers of depth filter material for capturing embolic particles;
   the filtering element being attached to the expandable strut assembly and being movable with the struts to expand and contact the wall of the body lumen, wherein blood flows through the filtering element to trap embolic particles released in the body lumen.

2. The filter device of claim 1, wherein the expandable strut assembly comprises:
   a proximal hollow cylindrical collar;
   a distal hollow cylindrical collar; and
   wherein the struts are joined to the proximal collar and taper radially outwardly from the proximal collar to from a proximal truncated cone section and continue longitudinally to form an elongated cylindrical section and taper radially inwardly to join the distal collar forming a distal truncated cone section.

3. The filter device of claim 2, further comprising:
   a rotatable shaft member having a proximal end and a distal end; and
   wherein the proximal collar of the expandable strut assembly is rotatably affixed to the shaft member and the distal collar is movable longitudinally along the shaft member.

4. The filter device of claim 3, wherein:
   the proximal collar is mounted between a pair of stop elements which prevent longitudinal movement of the proximal collar relative to the shaft member while permitting the filtering assembly to be rotatable on the shaft member.

5. The filter device of claim 4, wherein:
   at least one of the stop elements is made from a radiopaque material.

6. The filter device of claim 2, wherein:
   the strut assembly is made from a segment of tubing, portions of which are selectively removed to form each of the struts of the assembly.

7. The filter device of claim 1, wherein:
   the expandable struts are self-expanding.

8. The filter device of claim 1, wherein:
   the depth filter material is an open cell, porous polymer foam.

9. The filter device of claim 1, wherein:
   the layers of depth filtering material are open cell foam, each layer of open cell foam having a different filter density.

10. The filter device of claim 1, wherein:
    the filtering element includes a top layer and a bottom layer with a plurality of layers of depth filters therebetween, each subsequent lower layer having a filter density greater than the adjacent upper layer.

11. The filter device of claim 1, wherein:
    the depth filter material is formed from a material selected from the group consisting of polyurethane, polyester, PTFE, and polyethylene.

12. The filter device of claim 1, wherein:
    the depth filter material is formed from a felted polymer material.

13. The filter device of claim 12, wherein:
    the felted material is made from about 1 denier to about 3 denier polymer fibers.

14. The filter device of claim 12, wherein:
    the felted material has a density of about 8 ounces per square yard.

15. The filter device of claim 1, wherein:
    the depth filter material is felt from an adjacent layer, where each layer of felt has a different density.

16. The filter device of claim 15, wherein:
    the filter element includes a top felt layer and a bottom felt layer with a plurality of felt layers therebetween, each subsequent lower felt layer having a density greater than the adjacent upper layer.

17. The filter device of claim 16, wherein:
    the filter element is made from a material selected from the group consisting of polyurethane, polyester, PTFE, and polyethylene.

18. The filter device of claim 1, wherein:
    at least one layer of depth filter material has a different filter density than the other layers of depth filter material.

19. The filter device of claim 18, wherein:
    the layers of the depth filter material are aligned adjacent to each other to form a composite filtering element having areas with different filtering densities for filtering different sizes of embolic particles.

20. The filter device of claim 18, wherein:

the layers of the depth filter material are aligned behind each other in a longitudinal direction to form a composite filtering element having areas with different filtering densities for filtering different sizes of embolic particles.

21. The filter device of claim 1, wherein:

each layer of depth material is formed from filtering media creating a multiplicity of meandering passageways of particular pore size through which an embolic particle of smaller size must pass through in order to bypass the particular depth filter layer.

22. A filter device for capturing embolic particles released into a body lumen of a patient, comprising:

an inner shaft member having a proximal end and a distal end;

an expandable strut assembly having a proximal collar and a distal collar and a plurality of expandable struts connected therebetween, one of the collars being attached to the inner shaft member;

a filtering element having an inlet face and an outlet face and having a plurality of layers for capturing embolic material; and the filtering element being attached to the expandable strut assembly and being movable with the struts to expand to contact the wall of the body lumen, wherein blood flows through the filtering element and any embolic debris entrained in the blood is captured by the filter.

23. The filter device of claim 22, wherein:

the expandable struts of the strut assembly are adapted to move between a collapsed position and an expanded position.

24. The filter device of claim 22, wherein:

the proximal collar of the expandable strut assembly is rotatably affixed to the shaft member and the distal collar is rotatable and movable longitudinally along the shaft member.

25. The filter device of claim 22, further including:

an outer tubular member connected to the proximal collar wherein relative motion between the outer tubular member and the inner shaft member creates an axial force for moving the expandable struts between the collapsed and expanded positions.

26. The filter device of claim 22, wherein:

the proximal collar is mounted between a pair of stop elements for preventing longitudinal movement of the proximal collar relative to the inner shaft member while permitting the filtering assembly to be rotatable on the inner shaft member.

27. The filter device of claim 26, wherein:

at least one of the stop elements is made from a radiopaque material.

28. The filter device of claim 22, wherein:

at least one layer for capturing embolic material has a different filter density than the other layers for capturing embolic material.

29. The filter device of claim 28, wherein:

the layers for capturing embolic material are aligned adjacent to each other to form a composite filtering element having areas with different filtering densities for filtering different sizes of embolic material.

30. The filter device of claim 28, wherein:

the layers for filtering embolic material are aligned behind each other in a longitudinal direction to form a composite filtering element having areas with different filtering densities for filtering different sizes of embolic material.

31. The filter device of claim 22, wherein:

each layer of depth material is formed from filtering media creating a multiplicity of meandering passageways of particular pore size through which an embolic particle of smaller size must pass through in order to bypass the particular depth filter layer.

32. A filter device for capturing embolic materials released into a body lumen of a patient, comprising:

an inner shaft member having a proximal end and a distal end;

a filtering element having an inlet space and an outlet space and a plurality of layers of depth filter material for capturing embolic material, each layer of depth material being formed from filtering media which creates a multiplicity of meandering passageways of particular pore size through which an embolic particle of smaller size must pass through in order to bypass the particular depth filter layer; and means attached near the distal end of the inner shaft member and the filtering element to open the inlet space within the body lumen.

33. The filter device of claim 32, wherein:

the layers of depth filtering material are open cell foam, each layer of open cell foam having a different filter density.

34. The filter device of claim 32, wherein:

the depth filter is an open cell, porous polymer foam.

35. The filter device of claim 32, wherein:

the depth filter material is formed from a material selected from the group consisting of polyurethane, polyester, PTFE, and polyethylene.

36. The filter device of claim 32, wherein:

the depth filter material is formed from a felted polymer material.

37. The filter device of claim 32, wherein:

the filtering element includes a top layer and bottom layer of depth filtering material with a plurality of layers of depth filters therebetween, each subsequent lower layer having a filter density greater than the adjacent upper layer, the top layer being located at the inlet space of the filtering element.

38. The filter device of claim 28, wherein:

at least one layer of depth filter material has a different filter density than the other layers of depth filter material.

39. The filter device of claim 38, wherein:

the layers of the depth filter material are aligned adjacent to each other to form a composite filtering element having areas with different filtering densities for filtering different sizes of embolic particles.

40. The filter device of claim 38, wherein:

the layers of the depth filter material are aligned behind each other in a longitudinal direction to form a composite filtering element having areas with different filtering densities for filtering different sizes of embolic particles.

41. A filter device for capturing embolic particles released into a body lumen of a patient, comprising:

a shaft member;

an expandable strut assembly having a proximal collar and a plurality of expandable struts connected thereto, the proximal collar being mounted between a pair of stop elements located on the shaft member which prevent longitudinal movement of the proximal collar on the shaft member while permitting the expandable strut assembly to be rotatable on the shaft member; and a filtering element having a first filter and a second filter for capturing embolic particles, the filtering element being attached to the expandable strut assembly and movable with the struts to expand with the body lumen, wherein body fluid which may have embolic particles entrained therein flows initially through the first filter and subsequently through the second filter for filtering at least some of the embolic particles present in the body fluid.

42. The filter device of claim 41, wherein:

the first filter has a different filter density than the second filter.

43. The filter device of claim 42, wherein:

the first filter is aligned adjacent to the second filter to form a composite filtering element having areas with different filtering densities for filtering different sizes of embolic particles.

44. The filter device of claim 41, wherein:

the second filter is aligned behind the first filter in a longitudinal direction to form the composite filtering element having areas with different filtering densities for filtering different sizes of embolic particles.

45. The filter device of claim 42, wherein:

the filtering element includes another filter disposed between the first filter and the second filter which has a different filter density than the first filter and the second filter.

46. The filter device of claim 42, wherein:

the second filter has a filter density greater than the first filter.

47. The filter device of claim 41, wherein:

the expandable struts are self-expanding.

48. The filter device of claim 41, wherein:

at least one of the stop elements is made from a radiopaque material.

49. The filter device of claim 41, wherein:

the shaft member is a guide wire.

50. The filter device of claim 41, wherein:

the first filter and the second filter are depth filters.

51. The filter device of claim 50, wherein the depth filters are made from an open cell, porous polymer foam.

52. The filter device of claim 50, wherein:

the first filter has a different filter density than the second filter.

53. The filter device of claim 50, wherein:

each layer of depth material is formed from filtering media creating a multiplicity of meandering passageways of particular pore size through which an embolic particle of smaller size must pass through in order to bypass the particular depth filter layer.

* * * * *

UNITED STATES PATENT AND TRADEMARK OFFICE
CERTIFICATE OF CORRECTION

PATENT NO. : 6,558,405 B1
DATED : May 6, 2003
INVENTOR(S) : Peter R. McInnes It is certified that error appears in the above-identified patent and that said Letters Patent is hereby corrected as shown below:

Column 12,
Line 46, change "28", to read -- 32 --.

Signed and Sealed this

Second Day of September, 2003

JAMES E. ROGAN
*Director of the United States Patent and Trademark Office*